United States Patent [19]
Orjales-Venero et al.

[11] Patent Number: 5,296,469
[45] Date of Patent: Mar. 22, 1994

[54] NEW SULFATED DIOSMIN DERIVATIVE

[75] Inventors: Aurelio Orjales-Venero, Neguri; Ramon Mosquera-Pestana, Las Arenas, both of Spain

[73] Assignee: Fabrica Espanola de Productos Quimicos y Farmaceuticos, S.A., Leioa-Lamiaco, Spain

[21] Appl. No.: 22,571

[22] Filed: Feb. 25, 1993

[30] Foreign Application Priority Data

Feb. 25, 1992 [ES] Spain .................................... 9200414

[51] Int. Cl.$^5$ ...................... A61K 31/70; C07H 11/00; C07H 15/00; C07H 15/24
[52] U.S. Cl. ...................................... 514/27; 514/926; 514/927; 514/928; 536/8; 536/8.8; 536/17.1; 536/18.1; 536/118
[58] Field of Search .................. 514/27, 926, 927, 928; 536/8, 118, 8.8, 17.1, 18.1

[56] References Cited

U.S. PATENT DOCUMENTS 4,334,058  6/1982  Nair et al. ................................ 536/8
4,414,207  11/1983  Nair et al. ................................ 536/8
4,894,449  1/1990  Venero et al. ....................... 536/118

Primary Examiner—Marianne M. Cintins
Assistant Examiner—Margaret J. Page
Attorney, Agent, or Firm—Birch, Stewart, Kolasch & Birch

[57] ABSTRACT

The diosmin heptakis (hydrogensulfate) aluminum complex is described, as well as its preparation procedure, characterized by reacting one mole of diosmin with seven moles of a sulfating agent in a dry medium and treatment with an aqueous aluminum hydroxycloride solution of the diosmin heptakis (hydrogensulfate) sodium salt thus obtained. A description of pharmacological assays carried out to confirm the cytoprotective action of the product is included.

7 Claims, No Drawings

NEW SULFATED DIOSMIN DERIVATIVE

The present invention relates to the diosmin heptakis (hydrogensulfate) aluminum complex (formula I), useful in the treatment of ulcerous processes.

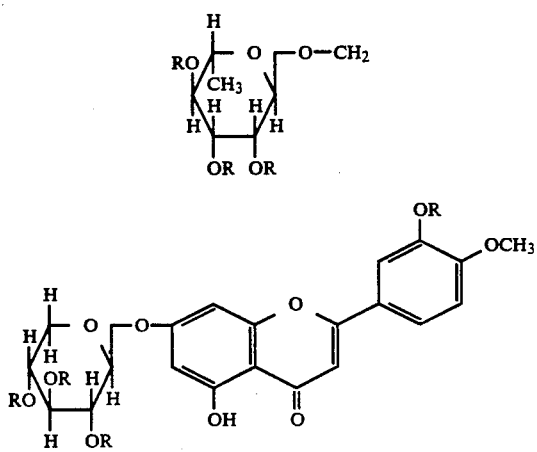

Formula I, R = $SO_3[Al_2(OH)_5]$
Formula II, R = $SO_3Na$

An earlier patent by the same authors (Spanish patent no. 8702270) describes the preparation of a related substance, the diosmin octakis (hydrogensulfate) aluminum complex, by reacting diosmin with an excess of a sulfating agent and treating the obtained product with aluminum hydroxychloride.

This invention relates to a new sulfated diosmin derivative obtained by a controlled reaction in anhydrous pyridine or alkylpyridine of one mole of diosmin with seven moles of a sulfating agent and isolated as the sodium salt (formula II) and as the aluminum complex (formula I). The molar ratio of the sulfating agent to diosmin is critical to obtain the diosmin heptakis (hydrogensulfate). The sulfating agent is selected from sulfur trioxide complexes with picolines and alkyl-substituted picolines, especially 2-picoline and 5-ethyl-2-picoline, which favour to control the process and afford exclusively the diosmin heptakis (hydrogensulfate), which is isolated as the sodium salt from the reaction medium and transformed into diosmin heptakis (hydrogensulfate) aluminum complex.

Both the sodium salt and the aluminum complex of the diosmin heptakis (hydrogensulfate) are of particular interest because of their pharmacological activities, especially the aluminum complex which has proved to be very effective as antiulcerous agent. The diosmin heptakis (hydrogensulfate) aluminum complex is a yellow solid, insoluble in water and organic solvents. Heated up to 350° C. it does not melt nor undergoes any changes. The diosmin heptakis (hydrogensulfate) sodium salt is a white solid which melts at 143°-6° C. The hydroxyl group which remains unsulfated is that of the 5 position (formulas I and II), as confirmed by proton nuclear magnetic resonance (NMR) determinations. Hydroxyls at 5 position in flavonoids are the least reactive in the molecule and the study published in Z. Naturforsch., 43c, 625-630 (1988), which refers to the preparation of sulfated derivatives of a group of flavonoids (kaempferol, quercetin, tamarixetin, rhamnetin, eupalitin, eupatolitin and veronicafolin), none of which has the said hydroxyl sulfated, is a good reference.

However, under appropriated reaction conditions, persulfation is achieved, as referred in the Spanish patent 8702270 for diosmin octakis (hydrogensulfate) and in international patent WO 82/00586 for rutin deca (hydrogensulfate) sodium salt. In any case, if one of the hydroxyls remains unsubstituted it is always that of the 5 position, as related also in the international patent WO 82/00586, which describes how, with appropriated reaction conditions, rutin nona (hydrogensulfate) sodium salt with the free hydroxyl at 5 position is obtained. A free hydroxyl at 5 position in a flavone is easily detected by means of NMR, because the corresponding proton appears at a very low field position, approximately at 12-13 ppm (K. R. Markham and T. J. Mabry, "The Flavonoids", J. Harborne, T. Marby and H. Marby Eds., page 69, Chapman and Hall Ltd., London (1975)). In the diosmin heptakis (hydrogensulfate) sodium salt NMR spectrum the 5 position hydroxyl appears at 13.1 ppm.

The following examples of the preparation of the sodium salt and the aluminum complex of diosmin heptakis (hydrogensulfate) illustrate the invention but are not exhaustive.

EXAMPLE 1

Diosmin Heptakis (Hydrogensulfate) Sodium Salt 60 ml of 5-ethyl-2-picoline are introduced into a reaction flask provided with a condenser and a pressure compensated separatory funnel. A nitrogen stream is continuously flushed through the system, while is externally ice-water cooled. Under good stirring 4.58 ml of chlorosufonic acid are added dropwise. Then 6 g of anhydrous diosmin are introduced in the flask and the mixture heated during 3 hours at 60° C. The solution is then neutralized with aqueous sodium hydroxyde solution to a pH of 7.0-8.0 and the two layers obtained are separated by using a separating funnel. The aqueous layer is washed with ethyl acetate and again separated, being the diosmin heptakis (hydrogensulfate) sodium salt precipitated by adding slowly and under stirring 20 ml of ethanol. The resulting solid is filtered and washed several times with ethanol and dried. It could be purified by dissolution in water and precipitation by adding ethanol. 7.1 g of the product are obtained, m.p. 143°-6° C.

| Elemental analysis for $C_{28}H_{25}Na_7O_{36}S_7$: | | |
|---|---|---|
| C | Na | S |
| Calculated (%) 25.43 | 12.17 | 16.93 |
| Found (%) 25.02 | 12.56 | 16.68 |

$^1$H NMR (DMSO-d6): δ13.1 (1H,s,5).

EXAMPLE 2

To a diluted aqueous solution of 13.4 g of diosmin heptakis (hydrogensulfate) sodium salt 95 ml of a 15% aluminum hydroxychloride aqueous solution are added. The solid which forms is filtered and washed several times with water, then suspended in water and pH adjusted between 5.5 and 6.5 with diluted aqueous sodium hydroxyde solution. The solid is filtered, washed with water and dried at room temperature under vacuum, yielding 16.8 g of the diosmin heptakis (hydrogensulfate) aluminum complex as a yellow solid. M. p.: It does not melt at 350° C.

| Elemental analysis for $C_{28}H_{60}Al_{14}O_{71}S_7$: | | | |
|---|---|---|---|
| | C | Al | S |
| Calculated (%) | 15.75 | 17.70 | 10.49 |
| Found (%) | 16.14 | 17.40 | 10.82 |

The diosmin heptakis (hydrogensulfate) aluminum complex has shown to be pharmacologically active in experimental gastric and duodenal ulcer models, induced by different mechanisms (acid gastric hypersecretion, non steroidal antiinflammatories, cysteamine, stress and cold, etc.). It also shows an excellent cytoprotection activity against gastric lesions induced by absolute ethanol, with a mechanism of action partially related to an increase in the synthesis and/or intraluminal release of protective prostaglandins.

The results of two pharmacological studies carried out with diosmin heptakis (hydrogensulfate) aluminum complex are described for illustrative purposes:

To study its protective action against indomethacin-induced gastric lesions in the rat the method of Brodie and col. (Toxicol. Appl. Pharmacol., 17, 615–624 (1970)) was used. Male Wistar rats weighing 220 g were used and gastric lesions were induced by oral administration of indomethacin (40 mg/kg) suspended in water. A control group received only water. Treated animals received the diosmin heptakis (hydrogensulfate) aluminum complex 30 minutes before inducing the lesions. In table I the obtained results are shown. Code F-316 corresponds to the diosmin heptakis (hydrogensulfate) aluminum complex.

TABLE I

F-316 action on indomethacin-induced gastric lesions, administered 30 minutes before the ulcerogenic agent.

| PRODUCT | DOSE mg/kg | LESION INDEX (mm) Mean ± S.D. | INHIBITION PERCENTAGE |
|---|---|---|---|
| VEHICLE | — | 0.00 | — |
| VEHICLE + INDOMETHACIN | 40 | 18.571 ± 1.98 | — |
| F-316 + INDOMETHACIN | 100 40 | 10.568 ± 3.37 | −43.09* |
| F-316 + INDOMETHACIN | 200 40 | 7.965 ± 2.26 | −57.11** |
| F-316 + INDOMETHACIN | 400 40 | 6.536 ± 2.75 | −64.85** |

*$p < 0.05$
**$p < 0.01$ according to Student's t test.

Diosmin heptakis (hydrogensulfate) aluminum complex action on oesophagic lesions caused by simultaneous ligation of the pylorus and the glandular-aglandular transition area of the stomach of the rat has been studied, according to the procedure of Nakamura and col. (Japan J. Pharmacol., 32, 445–456 (1982)). It has been verified that the diosmin heptakis (hydrogensulfate) aluminum complex significantly protects the oesophagic mucose against gastric juice induced lesions. In the same way, the disomin heptakis (hydrogensulfate) sodium salt also attains similar protection values. In table II are shown the obtained results. Code F-316 corresponds to diosmin heptakis (hydrogensulfate) aluminum complex and F-706 to diosmin heptakis (hydrogensulfate) sodium salt.

TABLE II

Effect of compounds F-316 and F-706 on acute oesophagic lesions induced by simultaneous ligation of the pylorus and the glandular-aglandular transition area in the stomach of the rat. Reference product: Aluminium hydroxide.

| Treatment | Dose (mg/kg) | Lesion grade | | | | | Lesion Index (LI) | Protection % |
|---|---|---|---|---|---|---|---|---|
| | | 0 | 1 | 2 | 3 | 4 | | |
| Vehicle | — | 1 | 1 | 1 | 1 | 16 | 87.5 | — |
| F-316 | 25 | 9 | 0 | 0 | 0 | 1 | 10 | 88.51 |
| | 50 | 10 | 0 | 0 | 0 | 1 | 0 | 100 |
| | 100 | 10 | 0 | 0 | 0 | 0 | 0 | 100 |
| Aluminium Hydroxide | 200 | 2 | 1 | 3 | 3 | 1 | 50 | 42.86 |
| F-706 | 25 | 7 | 1 | 1 | 1 | 0 | 15 | 82.8 |
| | 50 | 10 | 0 | 0 | 0 | 0 | 0 | 100 |
| | 100 | 10 | 0 | 0 | 0 | 0 | 0 | 100 |

Based on their pharmacological properties, the diosmin heptakis (hydrogensulfate) sodium salt and the diosmin heptakis (hydrogensulfate) aluminum complex both are useful in the therapy of ulcerous processes. They can be administered alone or formulated with appropriated excipients, using conventional pharmaceutical forms. Suitable pharmaceutical forms for oral administration include solid and liquid unit oral dosage forms such as tablets, capsules, suspensions, powders and the like, whereas for dermic application formulations as cream and ointment are preferred.

What is claimed is:

1. Diosmin heptakis hydrogensulfate aluminum complex with molecular formula

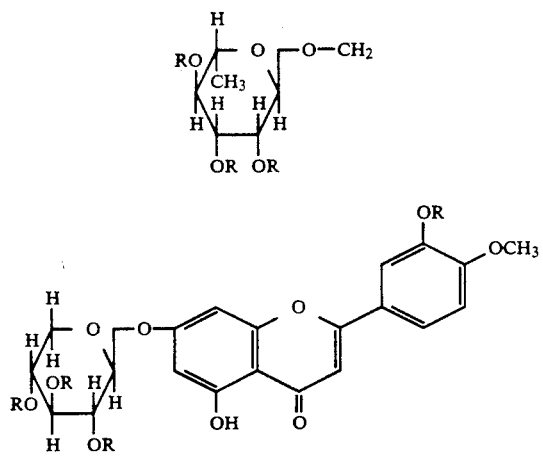

in which R represents $SO_3Al_2(OH)_5$.

2. A method of treating ulcerous lesions comprising administering to a patient in need thereof an effective amount of diosmin heptakis hydrogensulfate aluminum complex.

3. The method according to claim 2 wherein said ulcerous lesion is a gastric ulcer.

4. The method according to claim 2 wherein said ulcerous lesion is a duodenal ulcer.

5. The method according to claim 2 wherein said ulcerous lesion is a dermic ulcer.

6. A pharmaceutical composition which comprises an effective amount of a compound having the formula

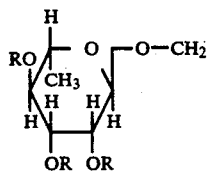
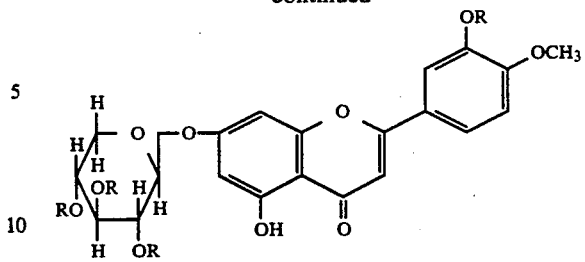
in which R is $SO_3Al_2(OH)_5$ and a pharmaceutically acceptable carrier.
7. The pharmaceutical composition according to claim 6, wherein said composition is a dermal cream or ointment.
* * * * *